United States Patent
Lee

(10) Patent No.: US 6,694,550 B2
(45) Date of Patent: Feb. 24, 2004

(54) CUSHION FOR RELIEVING FATIGUE AND REFORMING SLEEPING POSITION

(76) Inventor: Kwang-Ho Lee, 109-1103, Milkyway APT, Singok 2-dong, Uijeoungbu city Kyonggi-do (KR)

( * ) Notice: Subject to any disclaimer, the term of this patent is extended or adjusted under 35 U.S.C. 154(b) by 0 days.

(21) Appl. No.: 10/338,340

(22) Filed: Jan. 8, 2003

(65) Prior Publication Data

US 2003/0131414 A1 Jul. 17, 2003

(30) Foreign Application Priority Data

| Jan. 11, 2002 | (KR) | 20-2002-0000959 U |
| Jul. 31, 2002 | (KR) | 20-2002-0022998 U |
| Aug. 14, 2002 | (KR) | 20-2002-0024362 U |
| Dec. 18, 2002 | (KR) | 10-2002-0081469 |

(51) Int. Cl.[7] .............................................. A47C 20/00
(52) U.S. Cl. ..................... 5/632; 5/641; 5/652; 5/655.9
(58) Field of Search ........................ 5/632, 636, 641, 5/915, 652, 655.9; D6/601

(56) References Cited

U.S. PATENT DOCUMENTS

| 4,081,870 A | * | 4/1978 | Iannucci ........................ 5/652 |
| 5,007,410 A | * | 4/1991 | DeLaney ..................... 601/53 |
| 5,561,879 A | | 10/1996 | Everall .......................... 5/655 |
| 5,599,280 A | * | 2/1997 | Wolden ........................ 601/15 |
| 5,836,900 A | * | 11/1998 | Leventhal ..................... 601/57 |
| 6,024,407 A | * | 2/2000 | Eakin ....................... 297/217.4 |
| 6,050,265 A | * | 4/2000 | Richardson .................. 128/845 |
| 6,256,818 B1 | * | 7/2001 | Hughes .......................... 5/639 |
| 6,367,105 B1 | * | 4/2002 | Farley ............................ 5/630 |
| 6,378,150 B1 | | 4/2002 | Minegishi et al. ........... 5/652.1 |

FOREIGN PATENT DOCUMENTS

EP          11192833 A2    4/2002

* cited by examiner

Primary Examiner—Teri Pham Luu
(74) Attorney, Agent, or Firm—Seth Natter; Natter & Natter

(57) ABSTRACT

A vibrating cushion for relieving fatigue and reforming a sleeping position includes a cylindrical sponge carrying three motors. A controller controls the motors to generate vibrations. The cushion includes a frame having open ends with one end of the sponge fixed in the frame. A vessel receiving a battery is inserted into an end of the frame. A cap having a controller input and display covers the vessel. An aromatic case is mounted to the cap and an outer cover covers an inner cover and the frame. Hot or cold packs are detachably mounted to the outer cover. A user lies on his/her side while wrapping arms and legs around the cushion or placing legs on the cushion, whereby the spine becomes straight and blood circulation is improved.

12 Claims, 9 Drawing Sheets

CUSHION FOR RELIEVING FATIGUE AND REFORMING SLEEPING POSITION

BACKGROUND OF THE INVENTION

1. Field of the Invention

The present invention is directed to a cushion for relieving fatigue and reforming a sleeping position, whereby a user has a good sleep while being massaged upon going to sleep, thus easily relieving his or her fatigue and correcting his or her abnormal sleeping position.

2. Description of the Prior Art

In general, since a person sleeps using only beddings and a pillow, thereby assuming an abnormal sleeping position for a considerable period of time, he or she suffers from muscle pain and does not have a good sleep, thus not recovering from his or her fatigue. In addition, accumulated fatigue causes the sleeping position to be poor.

With a view to overcoming the above problems, people have tried other sleeping positions. For example, a person elevates his or her legs on a certain support, such as a pillow or a chair, or lies on his or her side while a pillow is held in his or her arms. However, the person feels hot in summer by holding a pillow in his or her arms or legs, and since the size of the pillow is typically small, the effects of relieving fatigue and reforming the sleeping position are not achieved.

SUMMARY OF THE INVENTION

Therefore, the present invention has an object of solving the problems encountered in the prior art and providing a cushion for relieving fatigue of a user and reforming the user's sleeping position, by which the user lies on his or her side while wrapping his or her arms and legs around the cushion, thereby maintaining the spine of the user in a straight position.

It is another object of the present invention to provide a cushion for relieving fatigue and reforming a sleeping position, which is advantageous in terms of promotion of blood circulation and massaging effect by applying mechanical vibrations from the cushion placed under the legs of the user to the user.

It is still another object of the present invention to provide a cushion for relieving fatigue and reforming a sleeping position, whereby the user has a good sleep.

It is a further object of the present invention to provide a cushion for relieving fatigue and reforming a sleeping position, having a simple cushion structure and a low manufacturing cost.

It is a still further object of the present invention to provide a cushion for recovering from fatigue and reforming a sleeping position which can be easily maintained and mended.

In accordance with a primary embodiment of the present invention, there is provided a cushion for relieving fatigue and reforming a sleeping position comprising a cylindrical sponge having a predetermined length; first, second and third driving motors placed in the sponge to apply mechanical vibrations to the body of a user for relieving fatigue; a controller for controlling the first, second and third driving motors to generate the mechanical vibrations; a cylindrical plastic frame produced through a molding process and having open ends so that one end of the sponge is inserted into and fixed in the plastic frame; an inner cover covering the sponge and first and second molded bodies of the plastic frame; a vessel inserted into an end of the plastic frame and receiving a battery therein; a cap covering an opening of the vessel and equipped with an input unit and a display unit of the controller; an aromatic case mounted to the cap and having an aromatic material therein for supplying the aroma of the aromatic material; and an outer cover covering the inner cover and the plastic frame.

In accordance with a second embodiment of the present invention, there is provided a cushion for relieving fatigue and reforming a sleeping position, comprising a cylindrical sponge having a predetermined length; first, second and third driving motors placed in the sponge to apply mechanical vibrations to the body of a user for relieving fatigue; a controller for controlling the first, second and third driving motors to generate the mechanical vibrations; a cylindrical plastic frame produced through a molding process and having open ends so that one end of the sponge is inserted into and fixed in the plastic frame; an inner cover covering the sponge and first and second molded bodies of the plastic frame; a vessel inserted into an end of the plastic frame and having a battery therein; a cap covering an opening of the vessel and equipped with an input unit and a display unit of the controller; an aromatic case mounted to the cap and having an aromatic material therein for releasing the aroma of the aromatic material; an outer cover covering the inner cover and the plastic frame; and a warming or cooling sheet having a plurality of pockets sewn on an internal surface thereof for accommodating hot or cold packs, and being detachably mounted to an external surface of the outer cover for emitting warmth or coolness.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, a description will be given of a cushion for recovering from fatigue and reforming a sleeping position according to a primary embodiment of the present invention, with reference to the attached drawings.

Figure 1:
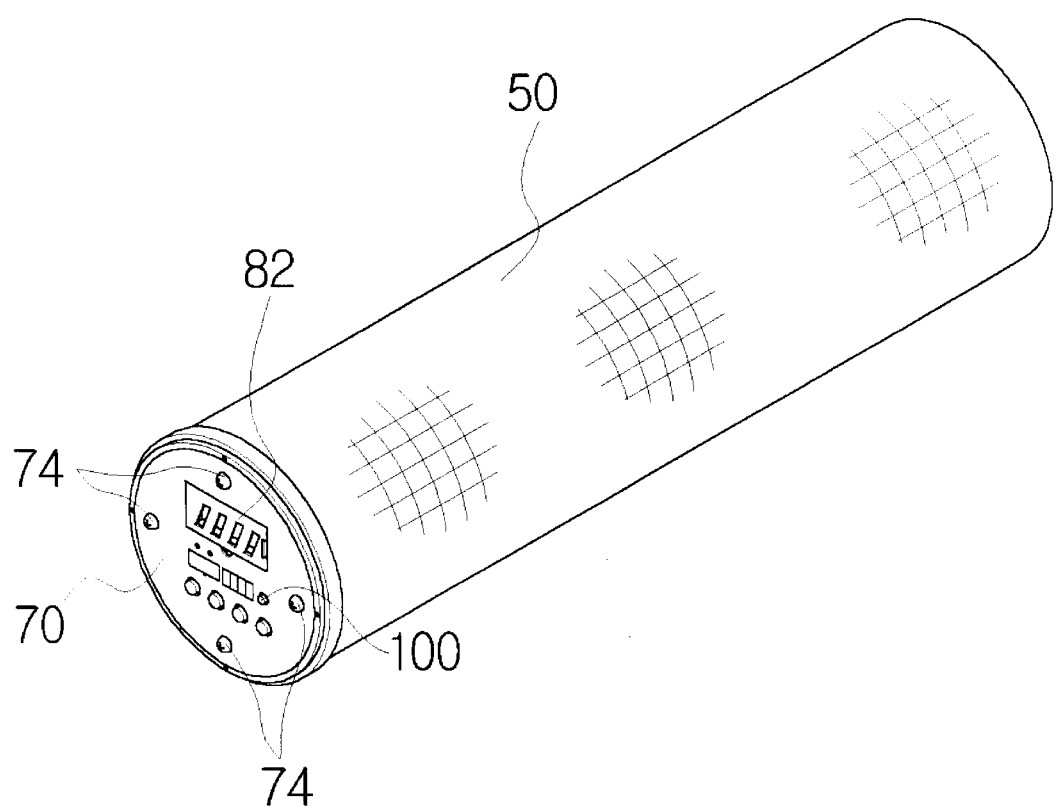
FIG. 1 is a perspective view schematically showing a cushion for relieving fatigue and reforming a sleeping position according to a primary embodiment of the present invention, before being covered with an outer cover.
Figure 2:
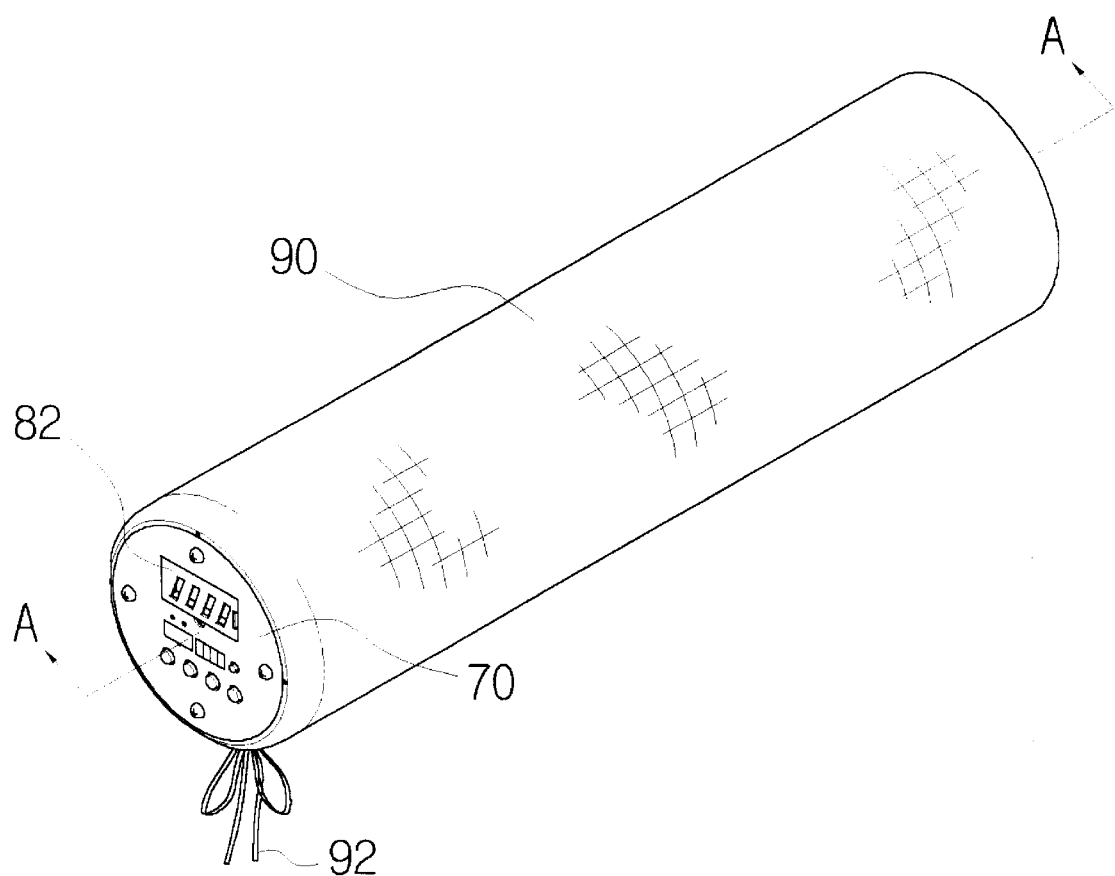
FIG. 2 is a perspective view schematically showing the cushion according to the present invention with the outer cover covering the cushion.
Figure 3:
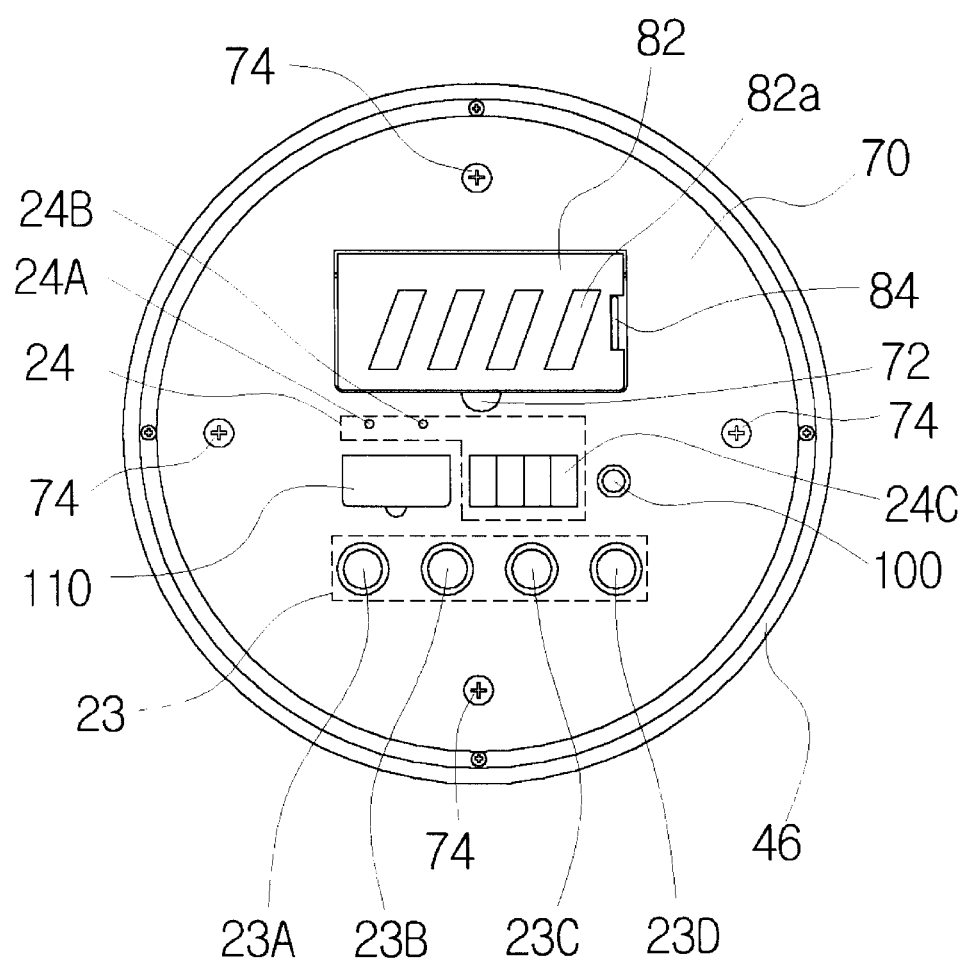
FIG. 3 is a front view of the cushion shown in FIG. 1.
Figure 4:
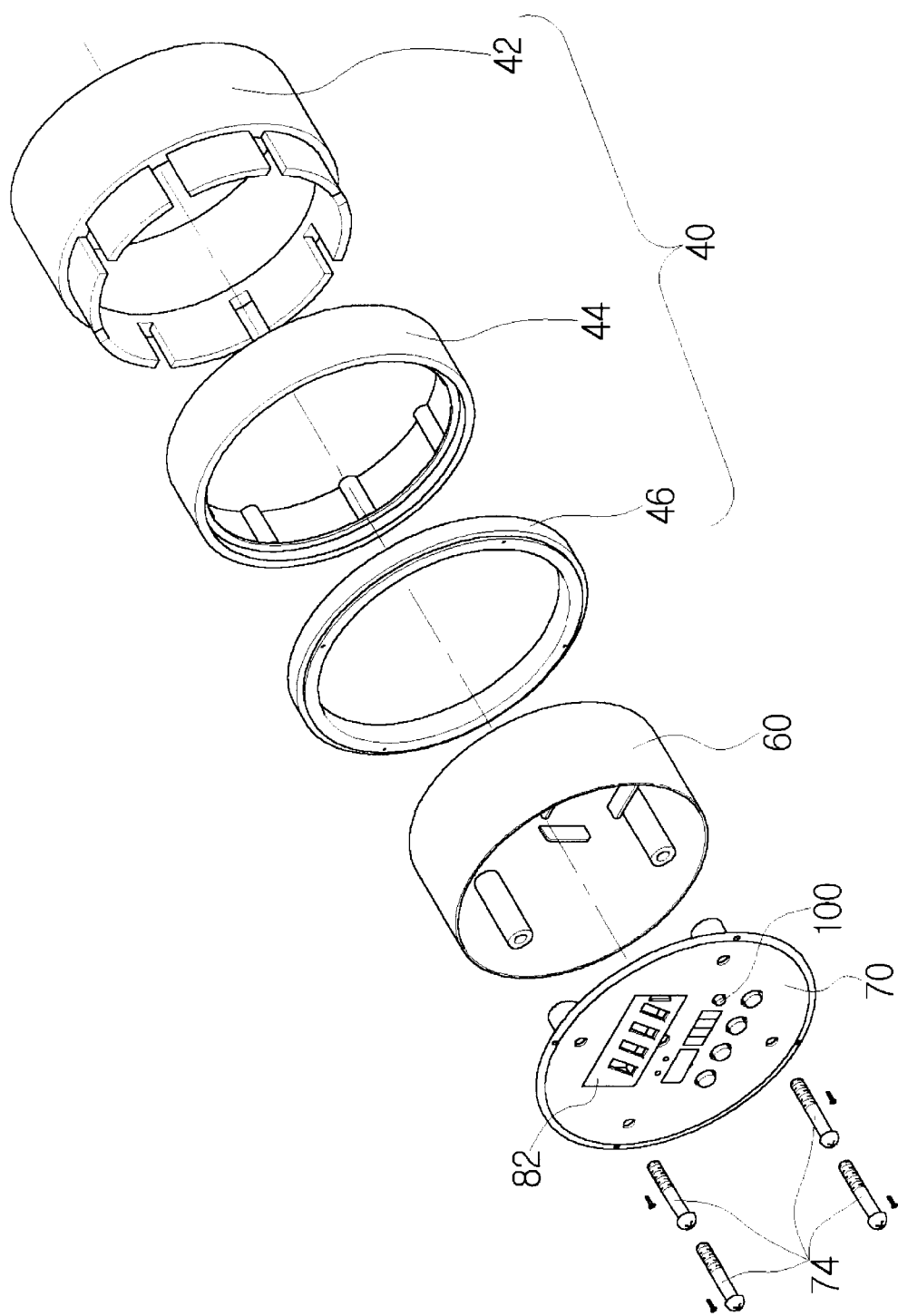
FIG. 4 is an exploded perspective view schematically showing a plastic frame used in the cushion according to the present invention.
Figure 5:
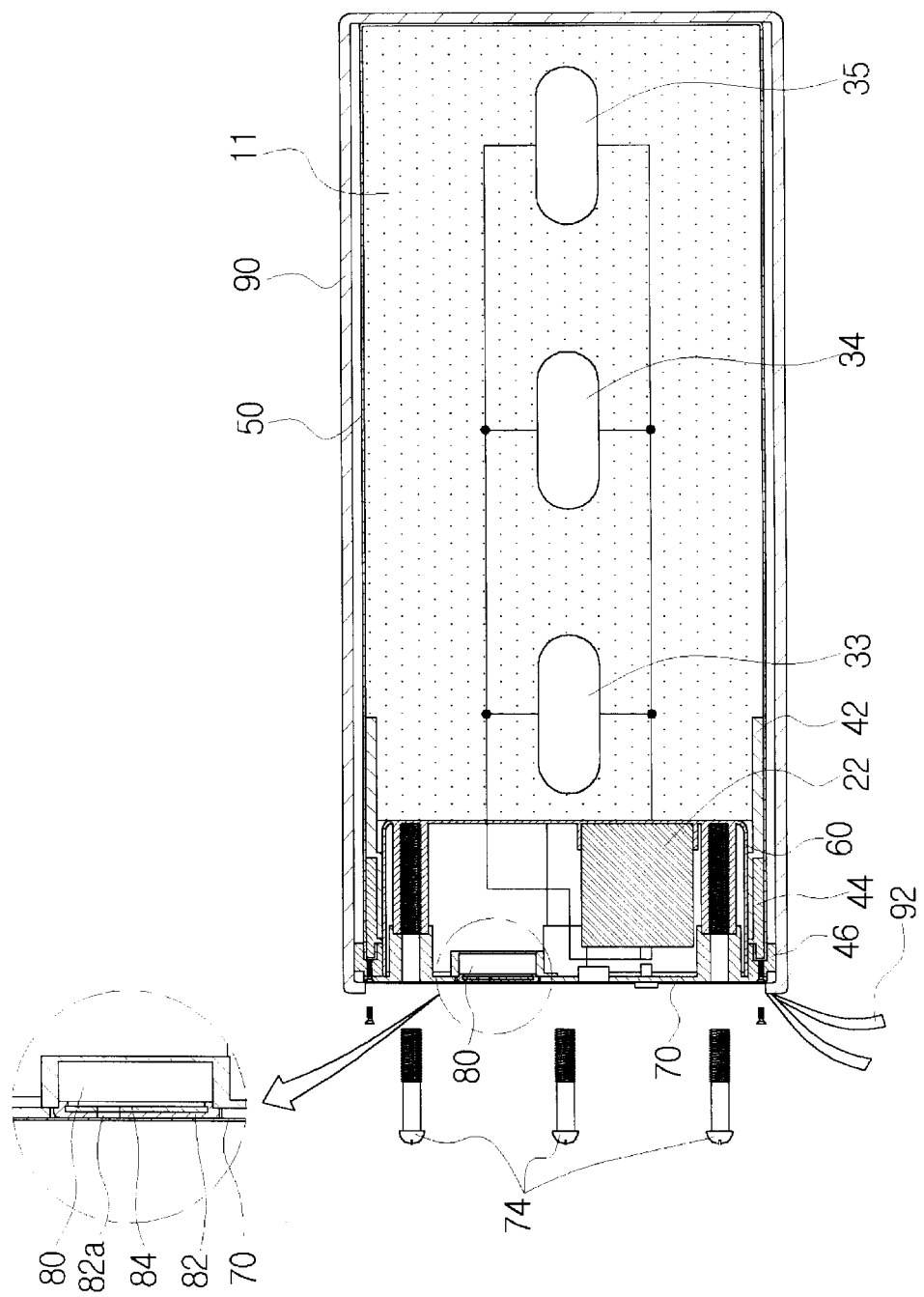
FIG. 5 is a longitudinal cross-sectional view showing the portion taken along an arrow A—A shown in FIG. 2.

Referring to FIG. 1, there is schematically shown an outer cover-removed cushion for relieving fatigue and reforming a sleeping position according to a primary embodiment of the present invention. FIG. 2 schematically shows the cushion according to the present invention with the outer cover covering the cushion. In addition, FIG. 3 shows a front view of the cushion shown in FIG. 1, and FIG. 4 schematically shows an exploded frame of the cushion according to the present invention. Further, a longitudinal cross-section of the portion taken along an arrow A—A shown in FIG. 2 is presented in FIG. 5, and a controller of the cushion is illustrated in FIG. 6 as a block diagram.

As shown in FIGS. 1 through 6, the cushion for relieving fatigue and reforming a sleeping position according to the primary embodiment of the present invention comprises a cylindrical sponge 11 having a predetermined length, first, second and third driving motors 33, 34 and 35 placed in the sponge 11 to apply mechanical vibrations to the body of a user, a controller 20 for controlling the first, second and third driving motors 33, 34 and 35 to cause the motors to generate the mechanical vibrations, and a cylindrical plastic frame 40 produced through a molding process and having open ends so that one end of the sponge 11 is inserted into and fixed in the plastic frame 40. In addition, the cushion further comprises an inner cover 50 covering the sponge 11 and first and second molded bodies 42 and 44 of the plastic frame 40, a vessel 60 inserted into an end (left side in FIG. 5) of the plastic frame 40 and receiving a battery 22 therein, and a cap 70 covering an opening of the vessel 60 and equipped with an input unit 23 and a display unit 24 of the controller 20. An aromatic case 80 is mounted to the cap 70 and has an aromatic material therein for releasing the aroma of the aromatic material, and an outer cover 90 covers the inner cover 50 and the plastic frame 40.

Figure 6:
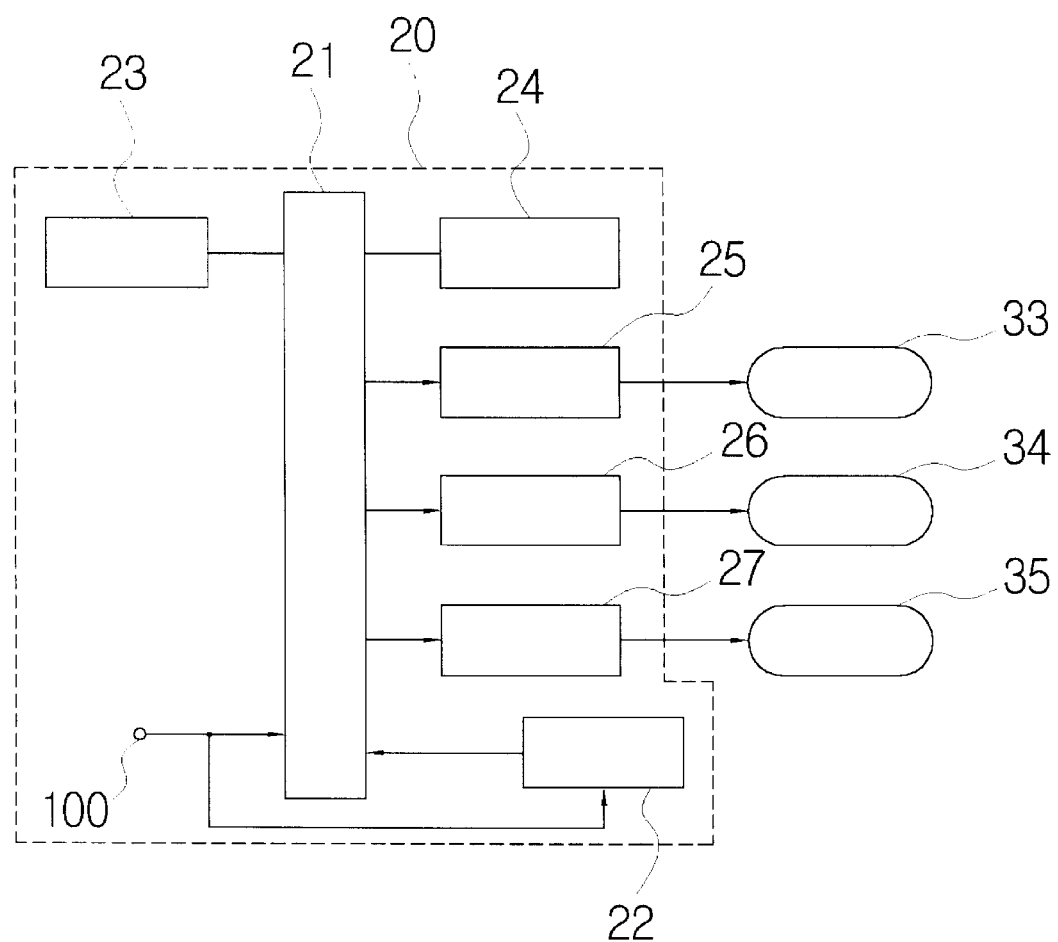
FIG. 6 is a block diagram schematically showing a controller of the cushion according to the present invention.

As presented in FIG. 6, the controller 20 includes a microprocessor 21 controlling operations of the motors, the battery 22 applying power required for operating the motors, the input unit 23 inputting instructions of the user to the microprocessor 21, and the display unit 24 displaying instructions of the user inputted by the input unit 23 and a charged state of the battery 22. Further, the controller 20 includes first, second and third drive units 25, 26 and 27 outputting drive signals so that at least one of the first, second and third driving motors 33, 34 and 35 is selectively driven for a predetermined time period in response to a control signal outputted from the microprocessor 21 when a manual button 23B of the input unit 23 is operated. The controller also includes a DC power jack 100 applying DC power from an external power source for charging the battery 22 and applying power required for performing the operations of the motors to the microprocessor 21.

The input unit 23 is comprised of a power button 23A applying electric power to the microprocessor 21 and the first, second and third driving motors 33, 34 and 35, and the manual button 23B inputting instructions of the user to the microprocessor 21 for manually controlling the first, second and third driving motors 33, 34 and 35 to operate the motors for a predetermined time period. In addition, the input unit 23 includes a strong button 23C inputting an instruction of the user for generating a strong vibration from the first, second and third driving motors 33, 34 and 35, and a weak button 23D inputting an instruction of the user for generating weak vibration from the first, second and third driving motors 33, 34 and 35.

The display unit 24 comprises a power display lamp 24A displaying power applied to the microprocessor 21 and the first, second and third driving motors 33, 34 and 35 upon switching-on of the power button 23A of the input unit 23. The display unit 24 also includes a manual mode display lamp 24B displaying power applied to the microprocessor 21 and a manual control mode for the first, second and third driving motors 33, 34 and 35 upon switching-on of the manual button 23B of the input unit 23, and a liquid crystal display 24C showing a charged state of the battery 22.

The inner cover 50 is formed in the shape of a bag with one opened side, comprising an inner gauze layer and an outer fabric layer coated with ceramic powders generating anions sewn together. One end of the inner cover 50 is wrapped around an open end of the second molded body 44 of the plastic frame 40 to be inserted into the open end and clamped by a clamp 46, thereby being locked to the plastic frame 40.

Additionally, the aromatic case 80 has a plurality of holes 82a formed on a lid 82 covering an opening thereof, with an opening ratio of the holes 82a being regulated by a slide plate 84 slidably mounted to an inner side of the lid 82 to control a release rate of the aroma. Also, the cap 70 is provided with a slot 72 to open and close the lid 82.

Preferably, the outer cover 90 is made of a woven fabric which is easily washable and has a desired softness. For instance, with the aim of keeping cool in summer, the outer cover 90 is made of hemp cloth or nonwoven fabric. Meanwhile, the outer cover 90 is made of materials retaining warmth, such as wool or synthetic fiber, for use in winter.

In the present invention, it is preferred that an eccentric motor is used as the first, second and third driving motors 33, 34 and 35.

In the drawings, the numeral 74 designates bolts for locking the cap 70 to the vessel 60, and the numeral 92 indicates a string fastening an open end of the outer cover 90 at the outside of the cap 70.

Thereafter, functions and effects of the cushion for relieving fatigue and reforming a sleeping position according to the primary embodiment of the present invention are described.

Upon going to bed, the user lies on his or her side while encircling the cushion with his or her arms and simultaneously wrapping his or her legs around the cushion. Then, when the power button 23A and the weak button 23D mounted to the input unit 23 of the controller 20 are switched-on, electric power is applied from the battery 22 to the microprocessor 21 and the applied power is displayed by the lighted power display lamp 24A (mainly using a light emitting diode (LED)) of the display unit 24.

In such case, drive control signals are outputted from the microprocessor 21 to the first, second and third drive units 25, 26 and 27 so that at least one of the first, second and third driving motors 33, 34 and 35 is sequentially driven by a control program stored previously in the microprocessor 21 of the controller 20. The first, second and third drive units 25, 26 and 27 which have received the drive control signals outputted from the microprocessor 21 output drive signals in order.

While the first, second and third driving motors 33, 34 and 35 are driven in response to drive signals outputted from the first, second and third drive units 25, 26 and 27, weak, vibrations are applied to the body of the user, thus massaging the body. Thereby, the user feels rested due to promotion of blood circulation. As well, the user becomes healthy due to skin massage. Additionally, the aroma of the aromatic material mounted into the aromatic case 80 is released through a plurality of the holes 82a formed on the lid 82 covering the opening of the case 80. Thus, the user may take a rest under a more pleasant relaxation or sleeping atmosphere.

In addition, when the user simultaneously wraps his or her arms and legs around the cushion, the spine of the user is generally straightened, thus reforming the sleeping position. Moreover, when the legs of the user are supported by the cushion, blood circulation in the legs is improved, whereby the user fully recovers from fatigue.

In a plurality of the holes 82a formed on the lid 82 covering the opening of the aromatic case 80, an opening ratio of the holes 82a may be regulated while the slide plate 84 slidably mounted to a back of the lid 82 is slid in left or right directions as shown in FIG. 3, thus controlling a release rate of the aroma.

The first driving motor 33, which is placed in the sponge 11, functions to massage the abdominal region of the user, and the second driving motor 34 in the sponge 11 acts to massage the groin. In addition, the third driving motor 35 is placed in the sponge 11 in order to massage the legs. Thereby, each body portion of the user may be easily massaged for a predetermined time period (for applying mechanical vibrations to the user, the above three driving motors may be simultaneously or sequentially driven).

While weak vibrations are applied to the user by the first, second and third driving motors 33, 34 and 35, the strong button 23C of the input unit 23 may be switched-on, whereby the first, second and third driving motors 33, 34 and 35 are operated to generate strong vibrations in response to drive signals outputted from the first, second and third drive units 25, 26 and 27.

When the manual button 23B of the input unit 23 is switched-on, operation of the first, second and third driving motors 33, 34 and 35 is manually controlled. Such operating condition is displayed by the lighted manual mode display lamp 24B (LED) of the display unit 24. Also, in response to drive signals outputted from the first, second and third drive units 25, 26 and 27 under control of the microprocessor 21, at least one of the first, second and third driving motors 33, 34 and 35 may be driven or all of the first, second and third driving motors 33, 34 and 35 may be simultaneously driven for a predetermined time period, thus promoting recovery from fatigue and reforming the sleeping position.

In case power charged to the battery 22 is completely consumed, a plug of an adaptor which is not shown is inserted into the DC jack 100, and DC power is applied to the microprocessor 21 and the battery 22. Thereby, under control of the microprocessor 21, at least one of the first, second and third driving motors 33, 34 and 35 may be driven or all of the first, second and third driving motors 33, 34 and 35 may be simultaneously driven, and also the battery 22 may be charged. When the battery 22 is replaced, a cap 110 covering a battery-accommodating chamber is opened and a spent battery may be easily replaced with a new battery.

In addition to using the cushion by holing it in arms of the user and putting one leg over a lower portion of the cushion, the cushion may be used as a support under the legs instead of a pillow, and thus the user may take a rest.

When the cushion is used as a support under the legs of the user, the heart and brain are positioned lower than the legs. Thus, blood from the legs is easily circulated to the heart and brain, and relief from fatigue may be further promoted.

Now, a description will be given of a cushion for relieving fatigue and reforming a sleeping position according to a second embodiment of the present invention, below.

Figure 7:
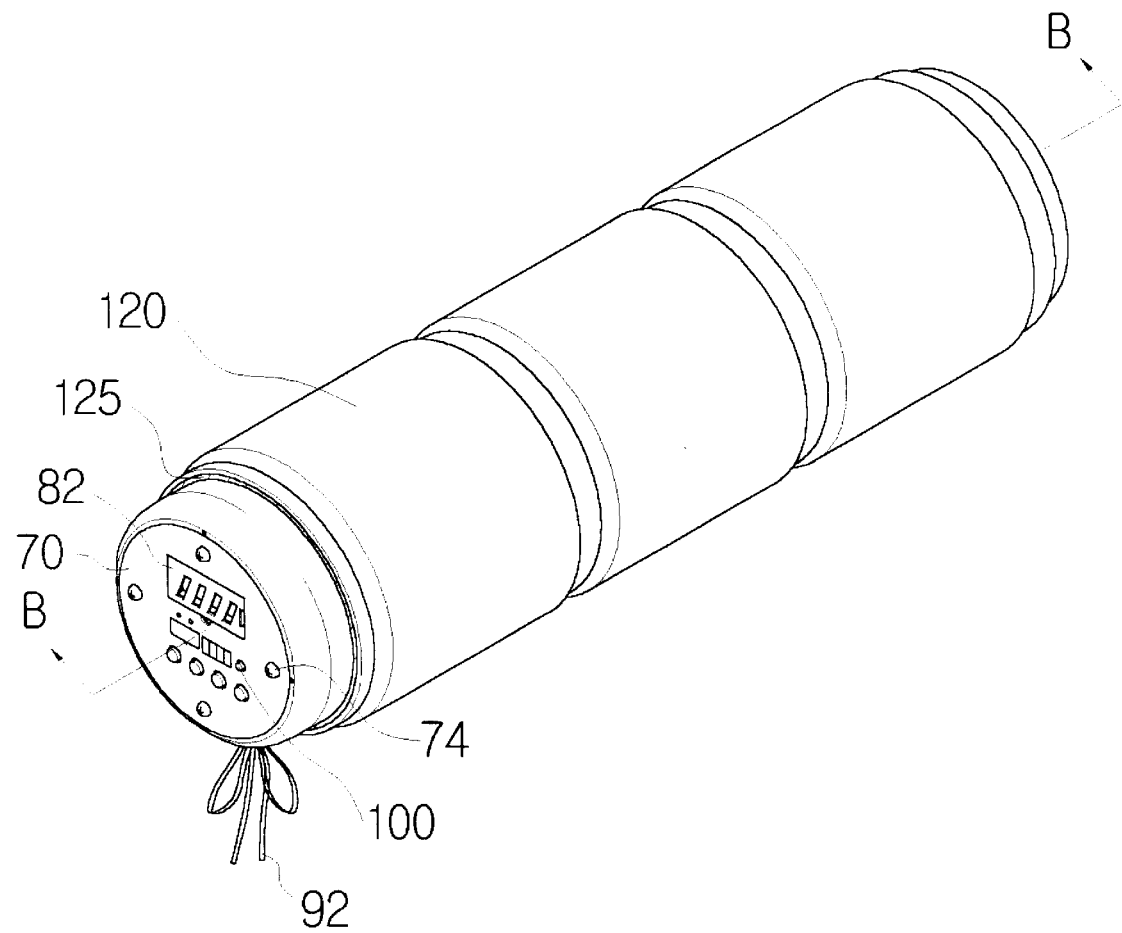
FIG. 7 is a perspective view showing a cushion for relieving fatigue and reforming a sleeping position according to a second embodiment of the present invention.
Figure 8:
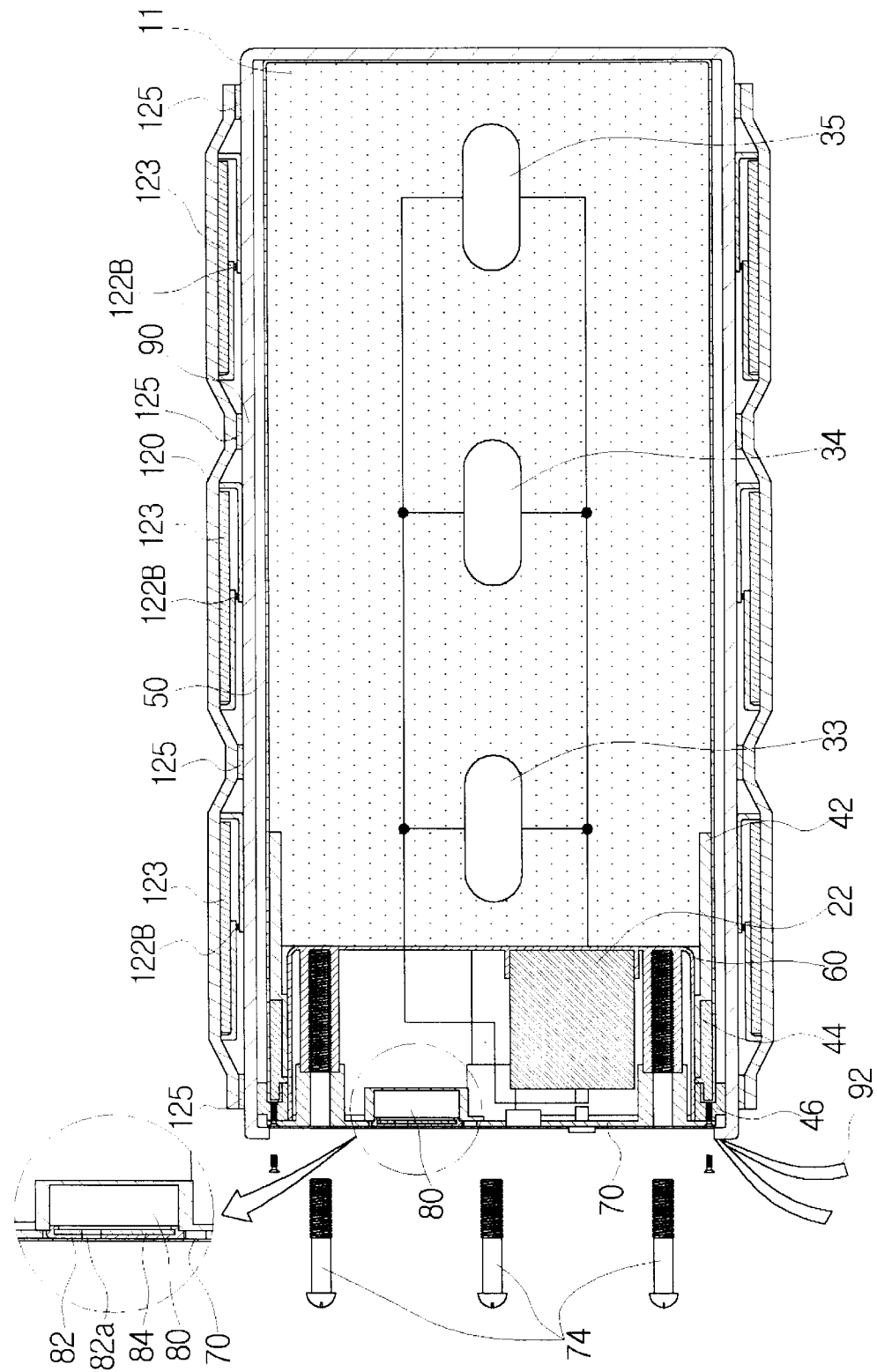
FIG. 8 is a longitudinal cross-sectional view of the portion taken along an arrow B—B shown in FIG. 7.
Figure 9:
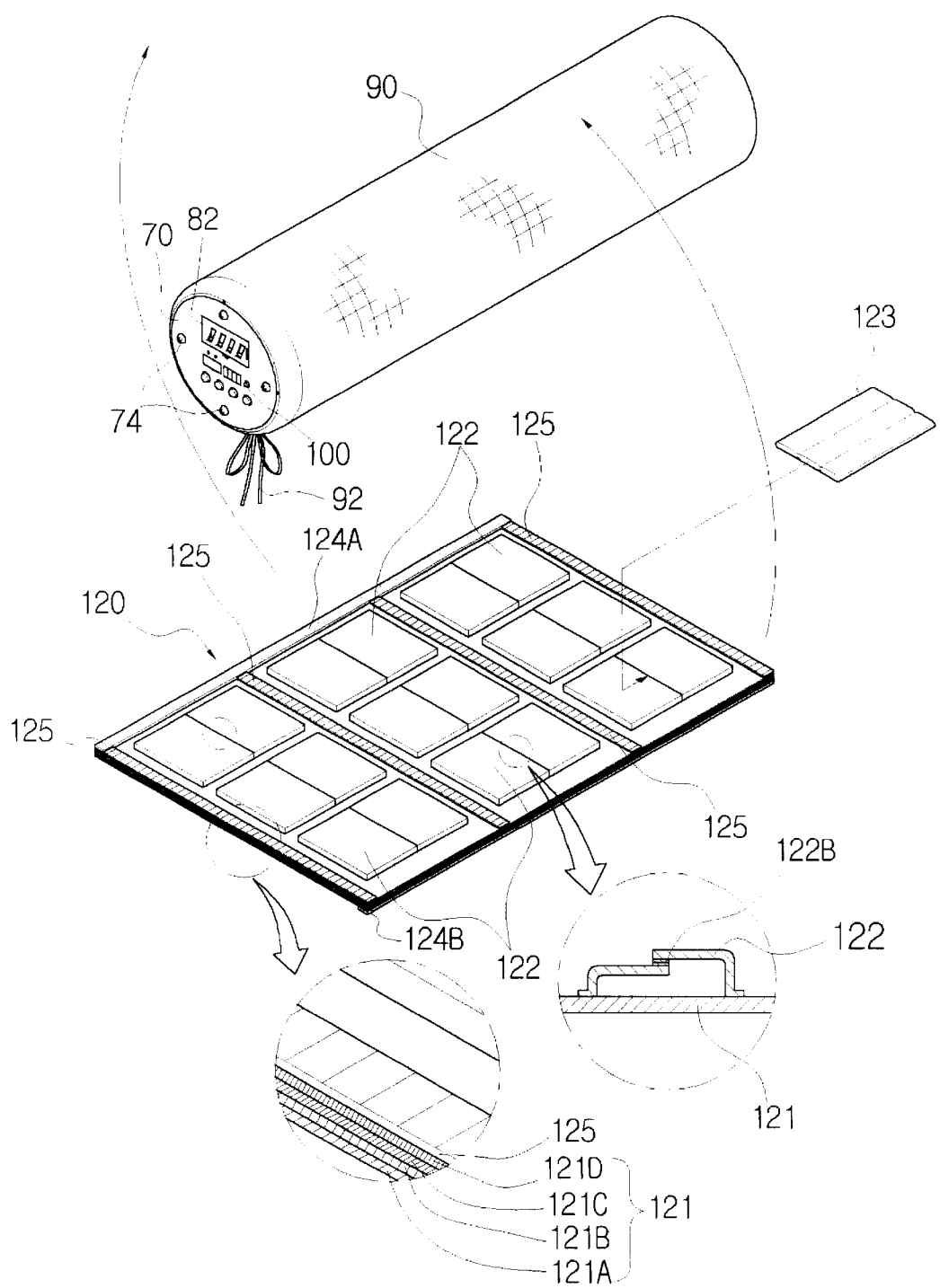
FIG. 9 is a perspective view schematically showing a warming or cooling sheet separated from the cushion of FIG. 7.

With reference to FIG. 7, there is shown a cushion for relieving fatigue and reforming a sleeping position according to a second embodiment of the present invention. FIG. 8 shows a longitudinal cross-section of the portion taken along an arrow B—B shown in FIG. 7, and FIG. 9 schematically shows a warming or cooling sheet separated from the cushion according to the second embodiment of the present invention. As for description of the cushion according to the second embodiment of the present invention, the same numerals designate the same parts as the cushion according to the primary embodiment of the present invention, and the repeated description thereof is omitted.

As shown in FIGS. 7 to 9, the cushion for relieving fatigue and reforming a sleeping position according to the second embodiment of the present invention comprises a cylindrical sponge 11 having a predetermined length, first, second and third driving motors 33, 34 and 35 placed in the sponge 11 to apply mechanical vibrations to the body of the user for relieving fatigue, and a controller 20 for controlling the first, second and third driving motors 33, 34 and 35 to cause the motors to generate the mechanical vibrations. The cushion also comprises a cylindrical plastic frame 40 produced through a molding process and having open ends so that one end of the sponge 11 is inserted into and fixed in the plastic frame 40, and an inner cover 50 covering the sponge 11 and first and second molded bodies 42 and 44 of the plastic frame 40. A vessel 60 is inserted into an end (left side in FIG. 8) of the plastic frame 40 and accommodates a battery 22 therein, and a cap 70 covers an opening of the vessel 60 and is provided with an input unit 23 and a display unit 24 of the controller 20. The cushion further includes an aromatic case 80 mounted to the cap 70 and having an aromatic material therein for supplying the aroma of the aromatic material, and an outer cover 90 covering the inner cover 50 and the frame 40. A warming or cooling sheet 120, having a plurality of pockets sewn on an internal surface thereof to accommodate hot or cold packs, is detachably mounted to an external surface of the outer cover 90 for emitting warmth or coolness to a user.

The cushion according to the second embodiment of the present invention is characterized by detachably attaching the warming or cooling sheet 120 to the external surface of the outer cover 90 of the cushion, different from the primary embodiment of the present invention, for emitting warmth or coolness to the user.

The warming or cooling sheet 120 includes a multi-layered fabric sheet 121, and a plurality of the pockets 122 sewn on an innermost waterproof fabric layer 121D of the multi-layered fabric sheet 121, with a slit 122A formed in each of the pockets 122. The hot or cold packs 123 are removably placed into the pockets 122 through the slits 122A and emit warmth or coolness to the user. In addition, the sheet 120 is composed of a Velcro fastener comprising hook and pile pieces 124A and 124B having a predetermined width and respectively mounted along the internal surface of a first longitudinal edge of the fabric sheet 121 and an external surface of a second longitudinal edge of the fabric sheet 121 for detachably attaching the warming or cooling sheet 122 to the outer cover 90. A plurality of elastic bands 125 are mounted at regular intervals to the internal surface of the fabric sheet 121 in a latitudinal direction so that the outer cover 90 is elastically compressed.

In the warming or cooling sheet 120, the multi-layered fabric sheet 121 is composed of an outermost waterproof fabric layer 121A for excluding moisture. An adiabatic nonwoven fabric layer 121B is placed on the waterproof fabric layer 121A for providing heat insulation, and a fiberglass layer 121C is layered on the nonwoven fabric layer 121B for preventing deterioration of the nonwoven fabric layer 121B. An innermost waterproof fabric layer 121D is superimposed on the fiberglass layer 121C for excluding moisture.

Functioning to fix the position of the hot or cold packs 123, a fastening unit 122B which is not shown in the drawings is mounted to the slit 122A of each of the pockets 122, and is exemplified by zipper, slide fastener, hook and pile pieces of Velcro fastener, and fastening string.

Here, functions and effects of the cushion for relieving fatigue and reforming a sleeping position according to the second embodiment of the present invention are described below.

The user lies on his or her side while holding the cushion in his or her arms and simultaneously wrapping one leg around a portion of the cushion upon going to sleep, after which the power button 23A and the weak button 23D mounted to the input unit 23 of the controller 20 are switched-on. Thereby, electric power is applied from the battery 22 to the microprocessor 21 and the applied power is displayed by the lighted power display lamp 24A (LED) of the display unit 24.

As such, drive control signals are outputted from the microprocessor 21 to the first, second and third drive units 25, 26 and 27 by a control program stored previously in the microprocessor 21 of the controller 20, whereby at least one of the first, second and third driving motors 33, 34 and 35 is sequentially driven. The first, second and third drive units 25, 26 and 27 which have received the drive control signals from the microprocessor 21 sequentially output drive signals.

While the first, second and third driving motors 33, 34 and 35 are driven in response to drive signals outputted from the first, second and third drive units 25, 26 and 27, weak vibrations are generated and the body of the user is massaged. Thereby, blood circulation is promoted and fatigue is relieved. As well, the user becomes healthy due to skin massage. Further, the aroma of the aromatic material mounted into the aromatic case 80 is released through a plurality of the holes 82a formed on the lid 82 covering the opening of the case 80. Thus, a pleasant relaxation or sleeping atmosphere is ensured.

Moreover, when the user lies on his or her side while encircling the cushion with his or her arms and wrapping his or her legs around the cushion, the spine of the user becomes generally straight, thus correcting the sleeping position. Also, blood circulation of the legs is improved, whereby the user may recover from fatigue.

As for the cushion according to the second embodiment of the present invention, the warming or cooling sheet 120 emitting warmth or coolness is detachably mounted to the external surface of the outer cover 90. Hence, for use in summer, cold packs 123 stored in a freezer are placed into the pockets 122 sewn on the internal surface of the multi-layered fabric sheet 121, after which the cooling sheet 120 is wrapped around and detachably attached to an external surface of the outer cover 90. Then, the hook piece 124A of the Velcro fastener having a predetermined width and mounted along the internal surface of the first longitudinal edge of the sheet 120 is attached to the pile piece 124B of the Velcro fastener having a predetermined width and mounted along the external surface of the second longitudinal edge of the sheet 120.

When the pile piece 124B of the Velcro fastener attached along the external surface of the longitudinal edge of the warming or cooling sheet 120 is combined with the hook piece 124A of the Velcro fastener attached along the internal surface of the longitudinal edge of the sheet 120, the elastic bands 125 mounted at regular intervals to the internal surface of the warming or cooling sheet 120 are tightly fitted to the outer cover 90 while firmly holding the cushion in place.

In the warming or cooling sheet 120, the hot or cold packs 123 emitting warmth or coolness are releasably placed into the pockets 122 formed on the innermost waterproof fabric layer 121D of the fabric sheet 121. For instance, a cooling sheet 120 provided with cold packs 123 is wrapped around the cushion, and the user holds such a cushion in his or her arms and puts one leg over a lower portion of the cushion. Thereby, coolness by the cold packs 123 placed in the pockets 122 of the cooling sheet 120 is emitted to the body of the user, thus relieving fatigue while refreshing the user in summer. Also, the spine of the user is maintained in a straight position. The mechanical vibrations generated by driving the first, second and third driving motors 33, 34 and 35 are applied to the body of the user, and thus the user may take an enjoyable rest and may go to sleep, and also may reform his or her sleeping position.

Meanwhile, hot packs 123 are placed into the warming sheet 120, and the user encircles the cushion covered with such a warming sheet 120 with his or her arms and legs. Thereby, warmth is emitted from the hot packs 123 placed in the pockets 122 of the warming sheet 120 to the body of the user, whereby the user may recover from fatigue while keeping himself or herself warm in winter. As well, the spine of the user becomes straight, and the mechanical vibrations generated by driving the first, second and third driving motors 33, 34 and 35 are applied to the body of the user. So, the user may take an enjoyable rest and may go to sleep, and reform the sleeping position.

The fabric sheet 121 of the warming or cooling sheet 120 blocks penetration of water by the outermost waterproof fabric layer 121A, and blocks entrance and exit of heat by the adiabatic nonwoven fabric layer 121B superimposed on the waterproof fabric layer 121A. In addition, deformation of the adiabatic nonwoven fabric layer 121B is prevented by the fiberglass layer 121C layered thereon. The innermost waterproof fabric layer 121D placed on the fiberglass layer 121C functions to prevent penetration of water. By such a layered configuration, even though the hot packs 123 in the pockets 122 of the warming sheet 120 are damaged, the user cannot but get burned.

Each slit 122A of the pockets 122 is provided with a fastening unit for fixing the position of the packs 123 which is not shown and is exemplified by zipper, slide fastener, hook and pile pieces of Velcro fastener, fastening string, as mentioned in the primary embodiment of the present invention, whereby the position of the packs 123 inserted into the pockets 122 of the warming or cooling sheet 120 is fixed.

In a plurality of the holes 82a formed on the lid 82 covering the opening of the aromatic case 80, an opening ratio of the holes 82a may be regulated while the slide plate 84 slidably mounted to a back of the lid 82 is slid in left or right directions as best seen in FIG. 3, thus controlling a release rate of the aroma.

While weak vibrations are applied to the user by the first, second and third driving motors 33, 34 and 35, the strong button 23C of the input unit 23 is switched-on, whereby the first, second and third driving motors 33, 34 and 35 are operated to generate strong vibrations in response to drive signals outputted from the first, second and third drive units 25, 26 and 27.

When the manual button 23B of the input unit 23 is switched-on, operation of the first, second and third driving motors 33, 34 and 35 is manually controlled. Such operating condition is displayed by the lighted manual mode display lamp 24B (LED) of the display unit 24. Also, at least one of the first, second and third driving motors 33, 34 and 35 may be driven or all of the first, second and third driving motors 33, 34 and 35 may be simultaneously driven for a predetermined time period in response to drive signals outputted from the first, second and third drive units 25, 26 and 27 under control of the microprocessor 21, thus relieving fatigue and reforming the sleeping position of the user.

After power charged to the battery 22 is completely consumed, a plug of an adaptor which is not shown is inserted into the DC jack 100 and DC power is applied to the microprocessor 21 and the battery 22. Thereby, at least one of the first, second and third driving motors 33, 34 and 35 may be activated or all of the first, second and third driving motors 33, 34 and 35 may be simultaneously activated, and also the battery 22 may be charged, under the control of the microprocessor 21. When the battery 22 is replaced, a cap 110 covering a battery-accommodating chamber is opened and a spent battery may be easily replaced with a new battery.

The battery-accommodating chamber is formed at an inside of the cap 70, but is not limited thereto. For instance, the battery-accommodating chamber may be located opposite the cap 70 covering the above plastic frame 40, and further the DC jack 100 may be mounted to a location opposite the cap 70 covering the plastic frame 40.

As described above, the present invention provides a cushion for relieving fatigue and reforming a sleeping position. The cushion comprises a cylindrical sponge having a predetermined length, and first, second and third driving motors placed in the sponge to apply mechanical vibrations to the body of the user for relieving fatigue. The cushion also includes a controller for controlling the first, second and third driving motors to generate the vibrations, and a cylindrical plastic frame produced through a molding process and having open ends so that one end of the sponge is inserted into and fixed in the plastic frame. An inner cover covers the sponge and first and second molded bodies of the plastic frame, and a vessel is inserted into an end of the plastic frame and receives a battery therein. A cap covers an opening of the vessel and is provided with an input unit and a display unit of the controller. An aromatic case is mounted to the cap and has an aromatic material therein for releasing the aroma of the aromatic material. And an outer cover covers the inner cover and the frame. A warming or cooling sheet, having a plurality of pockets sewn on an internal surface thereof to accommodate hot or cold packs, is detachably mounted to an external surface of the outer cover for emitting warmth or coolness to the user.

Upon going to sleep or resting, the user lies on his or her side while wrapping his or her arms and legs around the cushion of the present invention, whereby the spine of the user may be straightened, thus reforming the sleeping position of the user. Further, when the user rests his or her legs on the inventive cushion, blood circulation of the legs is improved by mechanical vibrations generated from the first, second and third driving motors. Therefore, the cushion of the present invention is advantageous in terms of low manufacturing cost, simple structure, easily reforming a sleeping position, providing a massaging effect, and being easy to maintain and mend.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A cushion for relieving fatigue and reforming a sleeping position, comprising:

a cylindrical sponge having a predetermined length;

first, second and third driving motors placed in the sponge to apply vibrations to the body of a user for relieving fatigue;

a controller for controlling the first, second and third driving motors to cause the motors to generate the vibrations;

a cylindrical plastic frame produced through a molding process and having open ends so that one end of the sponge is inserted into and fixed in the plastic frame;

an inner cover covering the sponge and first and second molded bodies of the plastic frame;

a vessel inserted into an end of the plastic frame and receiving a battery therein;

a cap covering an opening of the vessel and equipped with an input unit and a display unit of the controller;

an aromatic case mounted to the cap and having an aromatic material therein for releasing the aroma of the aromatic material; and an outer cover covering the inner cover and the plastic frame.

2. The cushion as defined in claim 1, wherein said controller comprises a microprocessor controlling operations of the motors; the battery applying power required for operating the motors; the input unit inputting instructions of the user to the microprocessor; the display unit displaying instructions of the user inputted by the input unit and a charged state of the battery; first, second and third drive units outputting drive signals so that at least one of the first, second and third driving motors is selectively driven for a predetermined time period in response to a control signal outputted from the microprocessor when a manual button of the input unit is operated; and a DC power jack applying DC power from an external power source for charging the battery and applying power required for operating the motors to the microprocessor.

3. The cushion as defined in claim 1, wherein said input unit comprises a power button applying electric power to the microprocessor and the first, second and third driving motors; a manual button inputting instructions of the user to the microprocessor for manually controlling the first, second and third driving motors to operate the motors for a predetermined time period; a strong button inputting an instruction of the user for generating a strong vibration from the first, second and third driving motors; and a weak button inputting an instruction of the user for generating a weak vibration from the first, second and third driving motors.

4. The cushion as defined in claim 1, wherein said display unit comprises a power display lamp showing power applied to the microprocessor and the first, second and third driving motors upon switching-on of a power button of the input unit; a manual mode display lamp showing power applied to the microprocessor and a manual control mode for the first, second and third driving motors upon switching-on of a manual button of the input unit; and a liquid crystal display showing a charged state of the battery.

5. The cushion as defined in claim 1, wherein said inner cover is formed in the shape of a bag, comprising an internal layer of gauze and an external layer of a fabric coated with ceramic powders generating anions sewn together.

6. The cushion as defined in claim 1, wherein one end of said inner cover is wrapped around an open end of the second molded body of the plastic frame to be inserted into said open end and clamped by a clamp, thereby being locked to the plastic frame.

7. The cushion as defined in claim 1, wherein said aromatic case has a plurality of holes formed on a lid covering an opening thereof, with an opening ratio of the holes being regulated by a slide plate slidably mounted to an inner side of the lid to control a release rate of the aroma, and said cap is provided with a slot to open and close the lid.

8. The cushion as defined in claim 1, wherein the outer cover is made of a woven fabric material which is easily washable and exhibits a desired softness.

9. The cushion as defined in claim 1, wherein the outer cover is made of hemp cloth or nonwoven fabric for use in summer.

10. The cushion as defined in claim 1, wherein the outer cover is made of wool or synthetic fiber for use in winter.

11. A cushion for relieving fatigue and reforming a sleeping position, comprising:

a cylindrical sponge having a predetermined length;

first, second and third driving motors placed in the sponge to apply vibrations to the body of a user for relieving fatigue;

a controller for controlling the first, second and third driving motors to cause the motors to generate the vibrations;

a cylindrical plastic frame produced through a molding process and having open ends so that one end of the sponge is inserted into and fixed in the plastic frame;

an inner cover covering the sponge and first and second molded bodies of the plastic frame;

a vessel inserted into an end of the plastic frame and receiving a battery therein;

a cap covering an opening of the vessel and equipped with an input unit and a display unit of the controller;

an aromatic case mounted to the cap and having an aromatic material therein for providing the aroma of the aromatic material;

an outer cover covering the inner cover and the plastic frame; and a warming or cooling sheet having a plurality of pockets sewn on an internal surface thereof for accommodating hot or cold packs, and being detachably mounted to an external surface of the outer cover for emitting warmth or coolness to a user.

12. The cushion as defined in claim 11, wherein said warming or cooling sheet comprises a multi-layered fabric sheet; the pockets sewn on an innermost waterproof fabric layer of the multi-layered fabric sheet, with a slit formed in each of the pockets; the hot or cold packs releasably placed into the pockets through the slits and emitting warmth or coolness to a user; a Velcro fastener comprising hook and pile pieces having a predetermined width and respectively mounted along the internal surface of a first longitudinal edge of the fabric sheet and an external surface of a second longitudinal edge of the fabric sheet for detachably attaching the warming or cooling sheet to the outer cover; and a plurality of elastic bands mounted at regular intervals to the internal surface of the fabric sheet in a latitudinal direction so that the outer cover is held firmly in place.

* * * * *